United States Patent [19]

Stoughton

[11] 3,969,516

[45] July 13, 1976

[54] COMPOSITION AND METHOD FOR TREATMENT OF ACNE

[75] Inventor: Richard B. Stoughton, Rancho Santa Fe, Calif.

[73] Assignee: Nelson Research & Development Company, Irvine, Calif.

[22] Filed: July 7, 1975

[21] Appl. No.: 593,641

Related U.S. Application Data

[63] Continuation-in-part of Ser. No. 533,617, Dec. 19, 1974, abandoned.

[52] U.S. Cl. ............................................... 424/181
[51] Int. Cl.² ...................................... A61K 31/71
[58] Field of Search ................................... 424/181

[56] References Cited

UNITED STATES PATENTS 3,155,580    11/1964    Bergy et al........................ 424/181

OTHER PUBLICATIONS

Chem. Abst., vol. 73 (1970)–102083d.

*Primary Examiner*—Stanley J. Friedman
*Attorney, Agent, or Firm*—Martin A. Voet

[57] ABSTRACT

There is disclosed a method for topical treatment of acne. The method involves topical treatment of a human suffering from acne with an effective amount of an antibiotic of the lincomycin family.

9 Claims, No Drawings

COMPOSITION AND METHOD FOR TREATMENT OF ACNE

RELATIONSHIP TO EARLIER FILED APPLICATIONS

This application is a Continuation-in-Part of U.S. Ser. No. 533,617 filed Dec. 19, 1974 now abandoned.

BACKGROUND OF THE INVENTION

Field of the Invention

The invention relates generally to topical treatment of acne. More particularly, the invention relates to a method for the topical treatment of acne vulgaris with antibiotics of the lincomycin family.

Acne is the name commonly applied to any inflammatory disease of the sebaceous glands; also acne vulgaris. Acne vulgaris is a common inflammatory disorder of the skin first appearing in early adolescence. Endocrinological factors are thought to be of prime importance in producing a hyperactivity of the sebaceous glands which leads to the condition. Acne lesions contain no pathogenic organisms, despite the presence of pus. Sebum, a liquid secreted by the sebaceous glands, is thought to contain an irritant factor that results in the production of comedones which form an integral part of the disease. *Corynebacterium acnes*, ordinarily a member of the normal flora of the skin, is found in quantity in some acne lesions. Some observers believe that *C. acnes* plays a part in the pathogenesis of the acne lesion. For example, it is known that oral administration of antibiotics such as tetracycline reduce the population of *C. acnes* in the skin.

Various therapeutic methods for treating acne have been attempted including topical antibacterials, e.g. hexachlorophene, and systemic antibiotics such as tetracycline and clindamycin. While the systemic antibiotic treatment have been effective, the topical antibacterial treatments have not been effective.

It has long been known that systemic treatment of acne is not preferred because of side effects resulting from saturation of the entire body with antibiotics and the fact that only the affected skin need be treated. However, despite a long-felt need for a topical treatment for acne, antibiotics generally have been used only sytemically to treat acne because it was not heretofore believed that antibiotics could be used effectively in the topical treatment of acne.

SUMMARY OF THE INVENTION

It has now unexpectedly been discovered that certain active antibiotics may be used topically in the treatment of acne.

The invention relates to a method for temporarily alleviating the signs and symptoms of acne by topically administering to humans or animals antibiotics of the lincomycin family. The foregoing method is carried out by topically administering to a human or animal an effective amount of a composition containing about 0.1 to about 10% by weight of an antibiotic of the lincomycin family.

DETAILED DESCRIPTION OF THE INVENTION

The term "antibiotic of the lincomycin family" is used herein to refer to a class of antibiotic originally elaborated by an actinomycete *Streptomyces lincolnensis*. These compounds and their methods of synthesis are shown in U.S. Pat. Nos. 3,086,912 and 3,155,580. The structural formula of lincomycin is as follows:

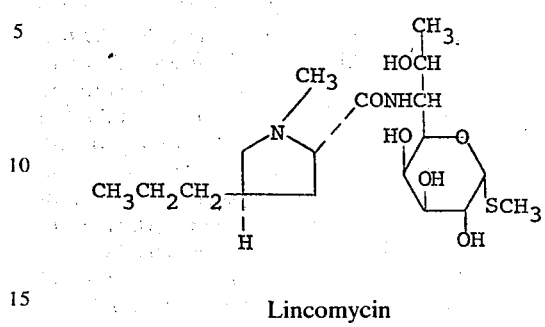

Lincomycin

Clindamycin is the 7-deoxy, 7-chloro derivative of lincomycin. Typical examples of antibiotics of the lincomycin family include lincomycin, mirincamycin, clindamycin, N-demethyl clindamycin and their pharmaceutically acceptable salts, e.g. clindamycin free base, clindamycin phosphate, clindamycin HCl, etc.

The amount of antibiotic of the lincomycin family which may be used in the present invention ranges from about 0.1 to about 10 percent by weight and preferably about 0.5 to about 5 percent by weight of the composition.

An effective amount of the composition, as the term is used herein, refers to that amount of composition which is effective therapeutically in the treatment of acne, especially acne vulgaris. The composition is generally applied about 1–4 times daily in conventional amounts, that is, amounts sufficient to thinly spread over the affected areas. The treatment is continued until or after all of the manifestations of acne have disappeared.

The antibiotics of the lincomycin family described herein may be dissolved in a suitable topical formulation and topically applied to affected areas of the skin in any convenient form, e.g. cream, lotion, spray, solution, etc.

Ingredients which may be used in these formulations include conventional formulating ingredients, such as, for example, Freons, ethyl alcohol, isopropyl alcohol, acetone, polyvinyl pyrrolidone, propylene glycol, fragrances, gel-producing materials, mineral oil, water, stearyl alcohol, stearic acid, spermaceti, sorbitan monooleate, Polysorbate 80, Tween 60, sorbital solutions, methylcellulose. Preferred ingredients include alcohols and other materials which enhance percutaneous absorption of antibiotics of the lincomycin family, including 2-pyrrolidone and N-lower alkyl substituted-2-pyrrolidones, e.g. N-methyl-2-pyrrolidone.

2-Pyrrolidone and N-lower alkyl-2-pyrrolidones are available commercially and are made by a number of methods known to those of skill in the art as exemplified by U.S. Pat. Nos. 2,555,353 and 2,267,757. N-lower alkyl-2-pyrrolidones include the straight and branch chain lower alkyl groups having 1–4 carbon atoms. N-methyl-2-pyrrolidone is preferred.

The amount of 2-pyrrolidone or N-lower alkyl-2-pyrrolidone which may be used in the present formulation ranges from about 5 to about 99.9 percent and preferably 10-50 percent by weight of the composition.

Following are specific examples which demonstrate the effectiveness of various forms of this invention.

EXAMPLE I

A clinical and microbiological study was carried out to show the effectiveness of the composition of the present invention in the treatment of acne. 5–6 human subjects with acne vulgaris were used in each determination. Formulations A, B and C (Table 1) were applied to each patient's face twice daily in an amount of about 0.5 cc per day. Comedones were removed with an extractor and put into a gelatin capsule. The capsule was dissolved in warm phosphate buffer and an aliquot plated on a special medium in dilutions which were cultured anaerobically for 7 days. The counts of C. acnes are expressed as the number of C. acnes per milligram of comedone material. Clinical appraisal was carried out at biweekly intervals. The results of the study are shown in Table 2 and 3 below.

Table 1

| Ingredients | A | B | C |
|---|---|---|---|
| Tetracycline HCl | 1% | — | — |
| Clindamycin phosphate | — | 1% | — |
| N-methyl-2-pyrrolidone | 99% | 99% | 100% |

Table 2

Antibacterial Evaluation of Antibiotics Active Against C. acnes in the Treatment of Acne Comedone Bacterial (C. acnes) Count, No./mg

| Preparation | Evaluation time, weeks | | | | |
|---|---|---|---|---|---|
| | 0 | 2 | 4 | 6 | 8 |
| A | $3\times10^7$ | $1\times10^7$ | $3\times10^6$ | $6\times10^6$ | $3\times10^7$ |
| B | $3\times10^6$ | $2\times10^5$ | $2\times10^3$ | $2\times10^1$ | $3\times10^1$ |
| C | $2\times10^6$ | $3\times10^6$ | $7\times10^5$ | $2\times10^6$ | $3\times10^7$ |

Table 3

Clinical Evaluation in the Treatment of Acne[a]

| Preparation | Evaluation time, weeks | | | | |
|---|---|---|---|---|---|
| | 0 | 2 | 4 | 6 | 8 |
| A | — | 0.7 | 1.0 | 0.8 | 1.1 |
| B | — | 2.2 | 3.1 | 3.5 | 3.5 |
| C | — | 0.5 | 0.6 | 0.7 | 0.9 |

[a]Appraisal based upon following scale:
0 = no response
1 = slight improvement
2 = good improvement
3 = very good improvement
4 = dramatic improvement The results of the foregoing tests show that formulation A (tetracycline) is essentially ineffective as is formulation C (a penetrating vehicle) alone. However, the results of the foregoing tests show a dramatic improvement with formulation B (a clindamycin together with a penetrating vehicle).

EXAMPLE II

Additional studies were performed with a clindamycin alone and with a clindaymcin with various vehicles to enhance percutaneous absorption. Each of the formulations shown in Table 1 was clinically tested in 15 acne patients over an 8-week period.

Table 1

| Ingredient | Formulation (%) | | | |
|---|---|---|---|---|
| | A | B | C | D |
| Clindamycin phosphate | 1.3 | 1.3 | — | — |
| Clindamycin base | — | — | 1 | 1 |
| N-methyl-2-pyrrolidone | 34 | — | 34 | — |
| Adjuvant solvent | | | | |

Table 1-continued

| Ingredient | Formulation (%) | | | |
|---|---|---|---|---|
| | A | B | C | D |
| topical solution qs. ad | 100 | 100 | 100 | 100 |

The results of the study showed substantial improvement in most patients as shown in Tables 2 and 3 below. Table 2 describes the results in terms of clinical evaluation of the patients.

Table 2

| Formulation | Clinical Evaluation: Initial vs Final | | |
|---|---|---|---|
| | Improved | Same | Worse |
| A | 13 | 2 | 0 |
| B | 12 | 2 | 0 |
| C | 13 | 2 | 0 |
| D | 7 | 8 | 0 |

Table 3 describes the results in terms of the bacterial count of the comedones at the end of the two-month study.

Table 3

| Formulation | Bacterial Count | |
|---|---|---|
| | Decrease to 0 | Not decreased to 0 |
| A | 11 | 3 |
| B | 6 | 7 |
| C | 6 | 9 |
| D | 5 | 7 |

The foregoing study demonstrates the effectiveness of the formulations tested in the treatment of acne.

EXAMPLE III

The studies of Example II are repeated using clindamycin HCl, lincomycin, N-demethyl clindamycin and mirincamycin in the place of clindamycin phosphate. Comparable results are obtained.

EXAMPLE IV

Example III is repeated, except that the N-methyl-2-pyrrolidone is replaced by each of 2-pyrrolidone, N-ethyl-2-pyrrolidone, N-propyl-2-pyrrolidone and N-isobutyl-2-pyrrolidone. Comparable results are obtained.

EXAMPLE V

The following cream formulations are prepared:

| | Creams (%) | | | |
|---|---|---|---|---|
| | A | B | C | D |
| Clindamycin | 1 | 1 | 1 | 1 |
| N-methyl-2-pyrrolidone | 25 | 20 | 34 | 42 |
| Stearyl alcohol | 12 | — | — | 10 |
| Stearic acid | — | 19 | 18 | 6 |
| Synthetic spermaceti | 7.5 | — | 2 | 4 |
| Sorbitan monooleate | 1.0 | — | — | — |
| Polysorbate 80 | 5.5 | — | — | — |
| Tween 60 | — | 3.5 | 3.5 | 3.5 |
| Arlacel 60 | — | 3.5 | 3.5 | 1.5 |
| Sorbitol solution | 5.5 | 19.4 | 14 | 10.5 |
| Mineral oil | — | 2 | — | — |
| Methocel 90 HG:100 | — | 0.2 | 0.2 | 0.2 |
| Fragrances | 0.2 | — | — | — |
| Sodium citrate | 0.5 | — | — | — |
| Water qs. ad | 100 | 100 | 100 | 100 |

EXAMPLE VI

The following solution formulations are prepared:

| | Solutions (%) | | | |
|---|---|---|---|---|
| | A | B | C | D |
| N-demethyl clindamycin | — | — | 1 | — |
| Clindamycin phosphate | 1 | — | — | 1 |
| Mirincamycin | — | 1 | — | — |
| N-methyl-2-pyrrolidone | — | — | — | 25 |
| Isopropyl myristate | 5 | 5 | 5 | — |
| Propylene glycol | — | — | — | 33 |
| Fragrance | 0.1 | 0.1 | 0.1 | 0.1 |
| Adjuvant solvent qs. ad 100% | ethanol | iso-propyl alcohol | acetone | iso-propyl alcohol |

EXAMPLE VII

An aerosol form of formulation A of Example VI is prepared by preparing the following mixture:

| formulation B | 25% |
|---|---|
| Freon[1] | 75% |

[1]Freon is 75/25 Freon 114/12.

EXAMPLE VIII

The following gel formulations are prepared:

| | Gel (%) | |
|---|---|---|
| | A | B |
| Lincomycin base | 1 | — |
| Clindamycin phosphate | — | 1 |
| Carbopol 934 | 1 | — |
| Carbopol 940 | — | 0.75 |
| Ethanol | 50 | 50 |
| Ethoxyl 16R | — | 2 |
| Diethanolamine | — | 0.5 |
| di-2(ethylhexyl)amine | — | 0.5 |

EXAMPLE VIII — Continued

| | Gel (%) | |
|---|---|---|
| | A | B |
| Water qs. ad | 100 | 100 |

I claim:

1. A method for temporarily alleviating the signs and symptoms of acne comprising topically administering to humans suffering from acne an effective amount of a composition comprising about 0.1 to about 10 percent percent by weight of an antibiotic of the lincomycin family.

2. The method of claim 1 wherein the antibiotic is selected from the group consisting of lincomycin and a pharmaceutically acceptable salt thereof.

3. The method of claim 1 wherein the antibiotic is selected from the group consisting of clindamycin and a pharmaceutically acceptable salt thereof.

4. The method of claim 1 wherein the antibiotic is selected from the group consisting of mirincamycin and a pharmaceutically acceptable salt thereof.

5. The method of claim 1 wherein the antibiotic is selected from the group consisting of N-demethyl clindamycin and a pharmaceutically acceptable salt thereof.

6. The method of claim 1 wherein the composition additionally contains about 5 to about 99.9 percent by weight of a compound selected from the group consisting of 2-pyrrolidone and N-lower alkyl-2-pyrrolidone.

7. The method of claim 6 wherein the N-lower alkyl substituent of the compound has 1–4 carbon atoms.

8. The method of claim 6 wherein the compound is N-methyl-2-pyrrolidone.

9. A method for temporarily alleviating the signs and symptoms of acne comprising topically administering to humans suffering from acne an effective amount of a composition comprising about 0.5 to about 5 percent by weight of an antibiotic selected from the group consisting of clindamycin and a pharmaceutically acceptable salt thereof.

* * * * *